(12) United States Patent
Xu et al.

(10) Patent No.: US 10,732,161 B2
(45) Date of Patent: Aug. 4, 2020

(54) GAS SENSORS WITH CONTACT PADS

(71) Applicant: United States of America as represented by the Administrator of NASA, Washington, DC (US)

(72) Inventors: Jennifer Xu, Westlake, OH (US); Gary W. Hunter, Oberlin, OH (US)

(73) Assignee: United States of America as Represented by the Administrator of National Aeronautics and Space Administration, Washington, DC (US)

( * ) Notice: Subject to any disclaimer, the term of this patent is extended or adjusted under 35 U.S.C. 154(b) by 265 days.

(21) Appl. No.: 15/971,784

(22) Filed: May 4, 2018

(65) Prior Publication Data

US 2018/0321210 A1    Nov. 8, 2018

Related U.S. Application Data

(63) Continuation of application No. 14/679,278, filed on Apr. 6, 2015, now Pat. No. 9,970,914.

(60) Provisional application No. 61/975,166, filed on Apr. 4, 2014.

(51) Int. Cl.
| | | |
|---|---|---|
| *G01N 33/00* | (2006.01) | |
| *H01L 29/47* | (2006.01) | |
| *G01N 33/22* | (2006.01) | |
| *G01N 27/12* | (2006.01) | |
| *G01N 27/02* | (2006.01) | |
| *H01L 21/04* | (2006.01) | |
| *H01L 29/16* | (2006.01) | |
| *H01L 29/872* | (2006.01) | |
| *H01L 29/66* | (2006.01) | |

(52) U.S. Cl.
CPC ......... *G01N 33/0036* (2013.01); *G01N 27/02* (2013.01); *G01N 27/129* (2013.01); *G01N 33/0047* (2013.01); *G01N 33/225* (2013.01); *H01L 21/0495* (2013.01); *H01L 29/47* (2013.01); *H01L 29/1608* (2013.01); *H01L 29/6606* (2013.01); *H01L 29/872* (2013.01)

(58) Field of Classification Search
CPC ... G01N 27/129; G01N 33/005; G01N 33/525
See application file for complete search history.

(56) References Cited

U.S. PATENT DOCUMENTS

| | | | |
|---|---|---|---|
| 5,518,601 A | 5/1996 | Foos et al. | |
| 5,595,646 A | 1/1997 | Foos et al. | |
| 5,813,764 A | 9/1998 | Visser et al. | |
| 6,068,748 A | 5/2000 | Berger et al. | |
| 6,413,792 B1 * | 7/2002 | Sauer ............... | B01L 3/502761 257/253 |

(Continued)

*Primary Examiner* — Blake A Tankersley
(74) *Attorney, Agent, or Firm* — Robert H. Earp, III; Helen M. Galus (57) ABSTRACT

Systems, methods, and other embodiments associated with gas detecting sensors. According to one embodiment, a gas sensor includes a metal layer, a barrier interlayer, a substrate layer, a first insulating layer, a conduction path, a contact pad, and a second insulating layer. The conduction path connects the metal layer to the contact pad. The second insulating layer prevents diffusion through the contact pad, the conduction path, or the metal layer. The sensor includes a wire bonded electrical connection to the contact pad such that voltage can be determined and/or applied.

20 Claims, 4 Drawing Sheets

(56) References Cited

U.S. PATENT DOCUMENTS

| | | |
|---|---|---|
| 7,237,429 B2 | 7/2007 | Monty et al. |
| 7,370,511 B1 | 5/2008 | Chen et al. |
| 7,389,675 B1 | 6/2008 | Hunter et al. |
| 7,993,506 B2 | 8/2011 | Nakano et al. |
| 8,001,828 B2 | 8/2011 | Hunter et al. |
| 8,373,175 B1 | 2/2013 | Okojie |
| 2001/0032784 A1 | 10/2001 | Chan |
| 2003/0057109 A1* | 3/2003 | Wang ................ G01N 27/4072 205/775 |

* cited by examiner

GAS SENSORS WITH CONTACT PADS

CROSS REFERENCE TO RELATED APPLICATIONS

This application is a Continuation Application claiming the benefit of priority from U.S. patent application Ser. No. 14/679,278, filed on Apr. 6, 2015, which claims priority to U.S. Patent application No. 61/975,166, entitled "SiC Based Hydrogen/Hydrocarbon Sensors with Contact Pads for High Temperature Applications" filed on Apr. 4, 2014, each of which is hereby incorporated by reference herein.

ORIGIN OF THE INVENTION

The invention described herein was made by employees of the United States Government and may be manufactured and used by or for the Government for Government purposes without the payment of any royalties thereon or therefore.

FIELD OF THE INVENTION

The invention is in the field of hydrogen and hydrocarbon sensing. In particular, hydrogen and hydrocarbon gas are detected using a microfabricated, miniaturized Schottky diode.

BACKGROUND

Silicon carbide (SiC) has shown great potential for harsh environment sensor applications. Unlike the electronic devices which typically use a stable and inert structure, SiC sensors include a sensitive sensing surface to respond to gases reaching the sensor surface and an inert contact pad for wire bonding. Stable operation of SiC-based Schottky diodes use a noble metal(s) on top of a noble metal oxide which are on top of a silicon carbide to form a diode. For example, a structure can be palladium on top of palladium oxide which is on top of silicon carbide (a Pd/PdOx/SiC structure). Other structures can be platinum on top of palladium oxide which is on top of silicon carbide (a Pt/PdOx/SiC structure) or platinum on top of platinum oxide on top of silicon carbide (a Pt/PtOx/SiC structure). The structure facilitates detection of hydrogen, hydrocarbons, and other gases at elevated temperatures as high as 600° C. The Schottky diodes use the noble metal oxide as a barrier layer between a noble metal and the substrate. For example, as discussed above, the noble metal oxides can be palladium oxides (PdOx) or platinum oxides (PtOx). The noble metal can be palladium (Pd) or platinum (Pt) or their alloys. The substrate can be silicon carbide (SiC). The noble metal oxide barrier layer prevents silicide-forming reactions between the precious metal and the substrate layers. Sensor testing has shown that a Pd/PdOx/SiC structure and a Pt/PdOx/SiC structure provide stable sensing of hydrogen and hydrocarbons at high temperatures, while operating over a wide range of temperatures. For example, such a diode sensor was tested at 450° C. for nearly 1500 hrs. Detection of hydrogen from room temperature to 500° C. was also achieved. Further it has been shown the diode sensor can measure hydrogen to the level of at least 250 parts per billion.

While having a sensor element operational at high temperatures is beneficial to make successful measurements, the sensors should be electronically connected to other devices that can record, display, or analyze the measurements. Previously, wire bonding was made directly on the diode surface so that the sensor could be connected to a device. However, the direct wire bonding compromises the integrity of the sensor surface, particularly for long term and high temperature sensing and results in changes in the sensing surface and/or deterioration of the sensing surface. Further, repeatable sensor performance from one sensor to the other is compromised.

In previously constructed sensors, the electrical connection is susceptible to defects in the substrate that affects the readout. Furthermore, an electrical connection made directly to the diode compromises the durability of the sensor. The electrical connection can also physically damage the sensor during operation in certain circumstances.

BRIEF DESCRIPTION

This brief description is provided to introduce a selection of concepts in a simplified form that are described below in the detailed description. This brief description is not intended to be an extensive overview of the claimed subject matter, identify key factors or essential features of the claimed subject matter, nor is it intended to be used to limit the scope of the claimed subject matter.

As discussed above, a stable sensor in application is dependent on accurate and dependable sensing. The accuracy and dependability is related to an electrical connection to a diode. Contact pads can be used as an intermediate between the electrical connection and the diode. Described herein are examples of systems, methods, and other embodiments associated with gas sensors with contact pads. The systems, methods, and other embodiments described herein relate to a gas sensor embodiment including a substrate, a metal layer, a first insulating layer, a contact pad, and a second insulating layer. A more stable electrical connection to the sensor, and in particular the metal layer, such as the top of a diode structure, is achieved using contact pads such that the electrical connection does not degrade the quality and performance of the sensor.

The following description and drawings set forth certain illustrative aspects and implementations. These are indicative of but a few of the various ways in which one or more aspects may be employed. Other aspects, advantages, or novel features of the disclosure will become apparent from the following detailed description when considered in conjunction with the drawings.

BRIEF DESCRIPTION OF THE DRAWINGS

The accompanying drawings, which are incorporated in and constitute a part of the specification, illustrate various systems, methods, and other embodiments of the disclosure. Illustrated element boundaries (e.g., boxes, groups of boxes, or other shapes) in the figures represent one example of the boundaries. In some examples one element may be designed as multiple elements or multiple elements may be designed as one element. In some examples, an element shown as an internal component of another element may be implemented as an external component and vice versa.

DETAILED DESCRIPTION

Embodiments or examples illustrated in the drawings are disclosed below using specific language. It will nevertheless be understood that the embodiments or examples are not intended to be limiting. Any alterations and modifications in the disclosed embodiments and any further applications of the principles disclosed in this document are contemplated as would normally occur to one of ordinary skill in the pertinent art. Described herein are examples of systems, methods, and other embodiments associated with gas sensors with contact pads.

Figures 1A, 1B, 1C:
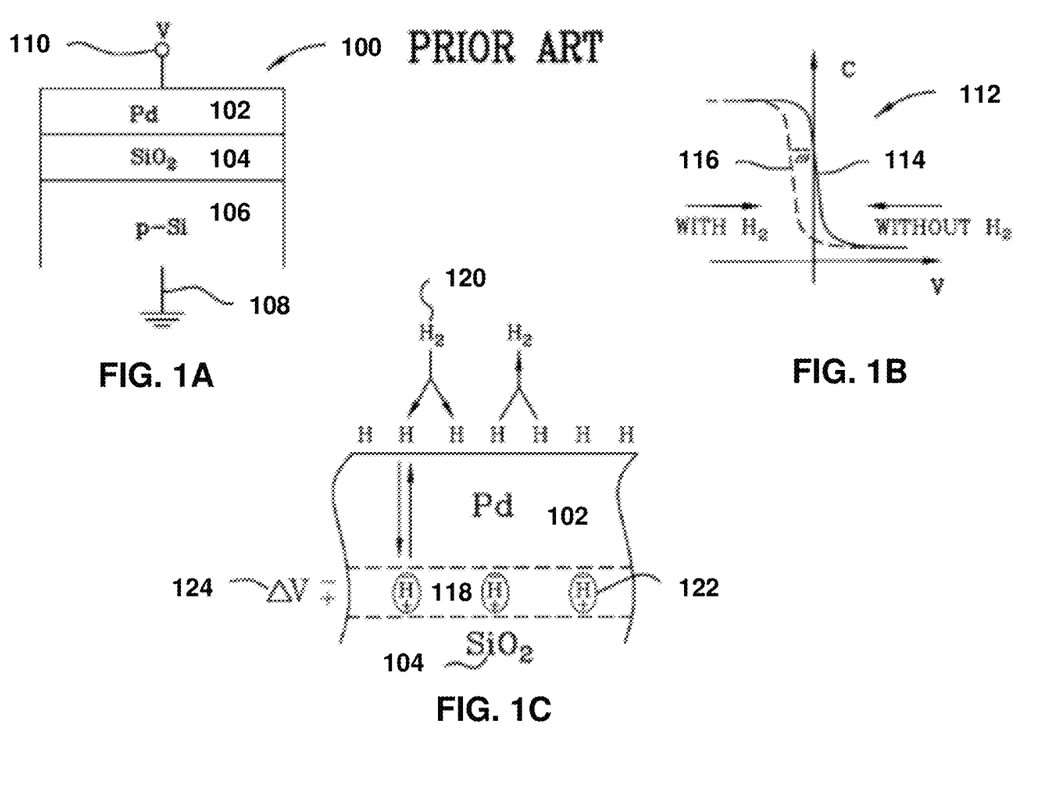
FIG. 1A is a schematic presentation of a prior art Pd/SiO2/Si hydrogen sensor.
FIG. 1B illustrates a shifting of the voltage-capacitance curve as a function of hydrogen content.
FIG. 1C illustrates a dipole layer formed at the interface of a metal and an insulator.

FIG. 1A illustrates a prior art example Pd/SiO2 hydrogen sensor 100 as described in U.S. Pat. No. 7,389,675 titled Miniaturized Metal (Metal Alloy)/PdOx/SiC Hydrogen and Hydrocarbon Gas Sensors, which is hereby incorporated by reference. Specifically, FIG. 1A illustrates an example structure of the hydrogen sensor 100 including a catalytic metal Pd 102, an insulator SiO2 104, and a Si substrate 106. The catalytic metal Pd 102 dissociates molecular hydrogen into atomic or elemental hydrogen H+. The elemental H+ forms a dipole layer at the interface of the Pd 102 and the insulator SiO2 104. The insulator SiO2 104 overlays the Si substrate 106. The Si substrate 106 is interconnected to a ground 108. A voltage 110 is supplied across the sensor 100 and functions as a capacitor.

FIG. 1B illustrates a voltage-capacitance (CV) curve as a function of hydrogen content. As the hydrogen content increases the magnitude of the CV shifts 112 or increases in proportion to the charge concentration and separation (for example, the dipole moment). The CV shift 112 translates to a change in voltage ($\Delta V$). Reference numeral 114 represents a CV curve without the presence of hydrogen and reference numeral 116 represents a CV curve with the presence of hydrogen.

FIG. 1C illustrates the dipole layer 118 formed at the interface of the Pd 102 and the insulator SiO2 104. As discussed above, hydrogen (H2) 120 is dissociated into elemental hydrogen (H+) 122. The magnitude of a dipole layer 118 is dependent on the amount of hydrogen available. The dipole layer 118 can be represented as a differential voltage 124.

Diodes with the structure of noble metal(s)/noble metal oxides/silica carbide have shown extended stability at high temperature environment. However, as discussed above, wire bonding was made directly on the diode surface, which can compromise the integrity of the sensor surface. As will be shown, by adding a contact pad to the diode, a complete sensor structure is formed without compromising the integrity of the sensor. Further, the complete sensor structure is packaging friendly. With the complete sensor structure, wire bonding can be made on the contact pad instead of on the diode surface so that the integrity of the sensor is not compromised. Compared to a photolithograph process for the fabrication of a diode without a contact pad, the fabrication of the complete sensor structure involves a multi-step fabrication process. The sensor can also detect hydrogen from room temperature to high temperatures, as well as hydrocarbons at elevated temperatures. The sensor may be used for fuel leak detection, fire detection, engine emission and environmental monitoring, and fuel cell safety applications.

Figures 2A, 2B:
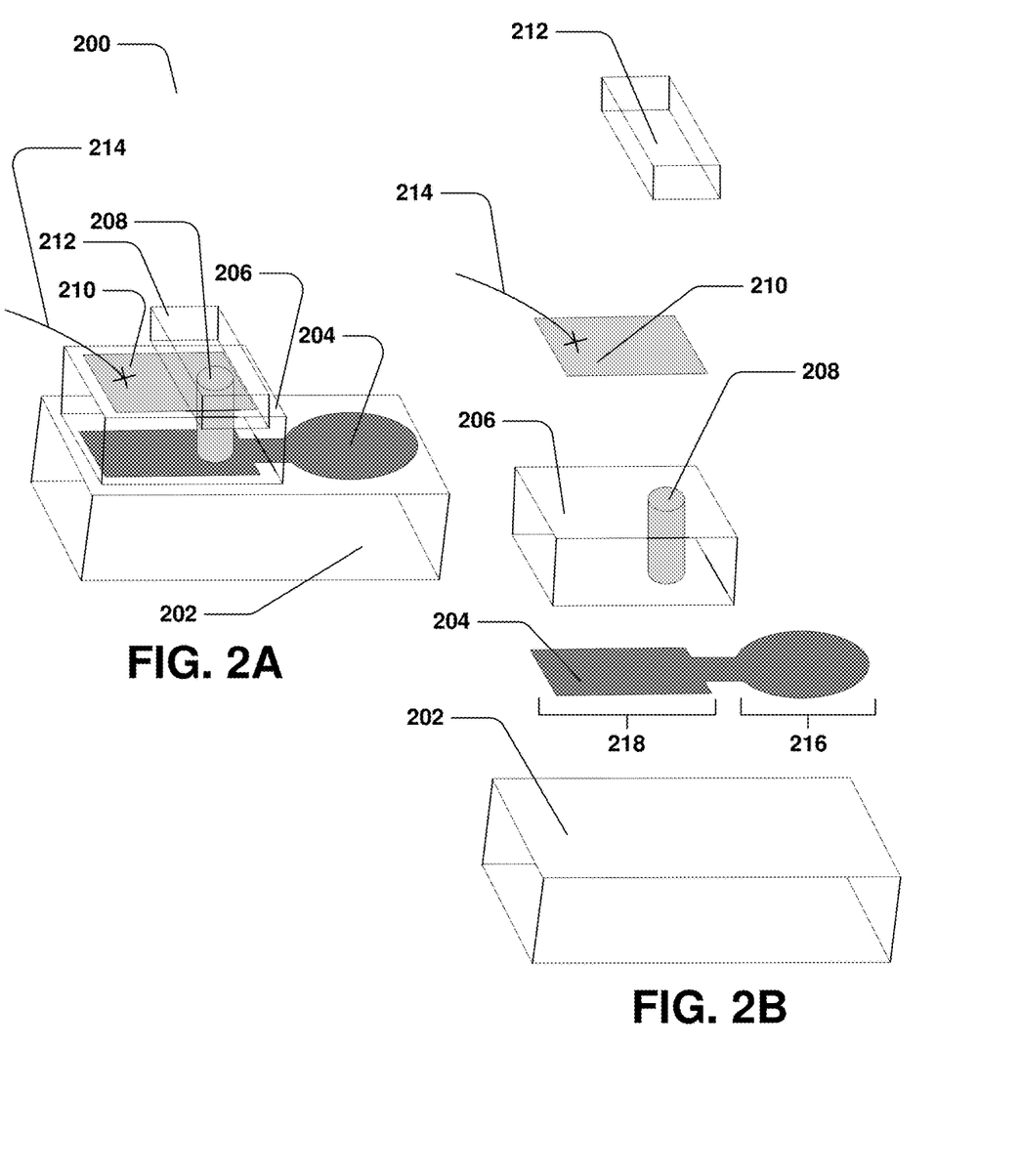
FIG. 2A illustrates one embodiment of a system associated with gas sensors with contact pads.
FIG. 2B illustrates an exploded view of the system of FIG. 2A associated with gas sensors with contact pads.

FIG. 2A is an illustration of one embodiment of a fabricated sensor 200 having multiple elements or layers to form a complete sensor. The fabricated sensor 200 includes a substrate layer 202, a metal layer 204, a first insulating layer 206, a conduction path 208, a contact pad 210, a second insulating layer 212, and an electrical connection 214.

FIG. 2B depicts an exploded view of the layers that make up the complete sensor 200. The sensor 200 includes a substrate layer 202. The substrate layer 202 can be of different compounds, such as SiC and or other semiconductors. The substrate layer 202 includes properties of a semiconductor. In one embodiment, the substrate layer 202 is a p-type or n-type semiconductor substrate layer.

The sensor 200 includes the metal layer 204 deposited on the substrate 202. In one embodiment, a metal oxide layer is deposited on the substrate in the same shape as the metal layer 204 between the metal and semiconductor to create a sensing junction between the metal layer 204 and the substrate 202. The structure of metal-oxide-semiconductor forms a diode for a thin oxide and one basis for sensing gas where an electrical change occurs in the diode when in the presence of the gas to be detected. To read the electrical change, electrical contacts are connected to the metal layer 204 and the substrate 202. In one embodiment, the metal layer 204 is deposited in a shape such that a sensing portion 216 is exposed to sense elements such as gas, and a contact portion 218 that is insulated from the sense elements. A electrical signal via an electrical connection to the contact portion 218 can be determined. As stated above, a direct electrical contact onto the metal layer 204 incurs problems. For example, the wire bonding can affect the contact material and inhibit viable and stable readouts from the metal layer 204. In one embodiment, the metal layer 204 is thin in comparison to the substrate layer 202 and the rest of the sensor.

The sensor 200 includes a first insulating layer 206 that shields the contact portion 218 of the metal layer 204 from outside elements such as the gas. The first insulating layer 206 prevents gas ions from diffusing into the metal layer 204 at the parts where the first insulating layer 206 covers the metal layer 204. The first insulating layer 206 is of sufficient thickness to prevent the gas ions from diffusing through it. In one embodiment, the first insulating layer 206 is thick in comparison to the metal layer 204. In one embodiment, the first insulating layer 206 is made of silicon oxide (SiO2) material.

The first insulating layer 206 includes an opened conduction path 208. The conduction path 208 may be deposited with electrically conductive material or compounds. The conduction path 208 provides a connection path between the metal layer 204 and a contact pad 210. The contact pad 210 can be made of any electrical conducting material. In one embodiment, the contact pad 210 and the conduction path 208 are made of the same material and form a single body. To form the single body including the contact pad 210 and the conduction path 208, the contact pad 210 and the conduction path 208 are deposited in the same step, which will be described in detail below. The contact pad 210 is shaped and sized such that it overlaps almost all or the entirety of the first insulating layer 206. The contact pad 210 is sized and shaped to overlap the top end of the conduction path 208. The contact pad 210 is of sufficient thickness to allow wire bonding to the surface of the contact pad 210. In one embodiment, the contact pad 210 is thick in comparison to the metal layer 204. The contact pad 210 is of sufficient thickness to prevent burnout of the metal layer 204 caused by an electrical connection overheating or damage during, e.g., the wire bonding process.

As discussed above the sensor 200 includes the second insulating layer 212. The second insulating layer 212 is sized and shaped to inhibits gas ions from diffusing through the contact pad 210 and the conduction path 208 and into the metal layer 204. For example, the second insulating layer 212 can overlap that area, and/or the surrounding area, of the contact pad 210 that is directly above the conduction path 208. Preventing diffusion and protecting the conduction path 208 allows for more accurate sensing by the diode. The second insulating layer 212 provides a complex diffusion barrier to help ensure that ions only diffuse through the sensing area of the metal layer 204. The second insulating layer 212 is of sufficient thickness to prevent the gas ions from diffusing through the second insulating layer 212. In one embodiment, the second insulating layer 212 can be of the same SiO2 material as the first insulating layer 206 or any other insulating material that prevents ions from diffusing.

The second insulating layer 212 is also sized and shaped for exposing a part of the contact pad 210 for an electrical connection. The sensor 200 includes an electrical contact 214 that is connected to the exposed portion of the contact pad 210 that is not covered by the second insulating layer 212.

FIGS. 3A, 3B, 3C, 3D, 3E, 3F, and 3G illustrate a top down view of a sequential sensor fabrication using masking techniques to form distinctly shaped layers that function in the sensor 200 as described above with respect to FIGS. 2A and 2B.

Figure 3A:
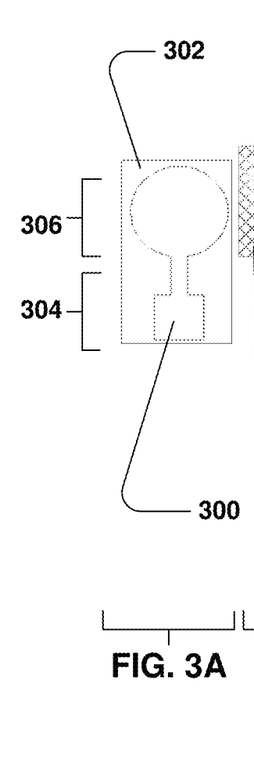
FIG. 3A illustrates an embodiment of a step in a fabrication process associated with gas sensors with contact pads.

With reference to FIG. 3A, a start point is a thin oxide and then metal layer 300 deposited on a substrate 302 and shaped with a contact area 304 and a sensing area 306 The metal layer 300 can be deposited on the substrate using different techniques including photolithography, sputtering, etc. In one embodiment, the metal layer 300 is deposited according to a controlled reactive sputter deposition (or evaporation) of approximately 50 Angstroms of Pd onto a target in an oxygen (O2) atmosphere on the SiC substrate layer 302 to form a PdOx barrier layer. Then a sputter deposition of 450 Angstroms of a metal or metal alloy selected from the group consisting of Pt, Pd, Au, Ir, Ag, Ru, Rh, In, Os, Cr, Ti, and alloys of these metals with each other is used on top of the PdOx barrier layer. Alternatively, in one embodiment, PdOx can be evaporated onto the SiC substrate 302. A range of other oxide or nitrides can be used rather than PdOx. Lift off processes and etchings are employed to remove masks and dictate size and shape of layers. The O2 atmosphere may be withheld for a few seconds to prevent the formation of silicon dioxide on the SiC substrate 302.

In one particular embodiment, constructing the metal layer 300 on the substrate layer 302 includes a metal(s) layer, a PdOx (oxide barrier layer), and a SiC (substrate layer) with an applied direct current voltage. In one example, the metal layer is a coating applied to the substrate. The metal layer 300 is a catalytic sensing metal. The metal layer 300 is located directly on top of a barrier interlayer and is in contact with the barrier layer. The metal layer 300 has a thickness of approximately 450-500 Angstroms but could be as thick as 1000 Angstroms. The oxide barrier interlayer is located next to the metal layer 300 and is approximately 50 Angstroms thick in the metal layer 300 embodiment. This enables electron tunneling and electrical conduction to occur through the diode in either a forward direction or a reverse direction. PdOx is non-conductive unless used in thin applications such as 50 Angstroms thick. In one embodiment, an amp meter measures the current in the diode at a constant voltage. The detection voltage in the forward bias sense is approximately 0.3 to 1.0 VDC.

In one embodiment, the semiconductor used herein is preferably of the polytype SiC which has surface characteristics conducive to receiving PdOx thereupon in a controlled and uniform manner. The PdOx barrier layer prevents a reaction between the catalytic metal and the SiC thus preventing degradation of the sensor and the formation of silicides.

Immediately underneath the barrier layer is the substrate layer 302. The substrate layer 302 may extend past the barrier layer in the horizontal direction for use in different applications such as a MOSFET transistor application.

As used herein barrier is referred to as a chemical reaction barrier. In particular the PdOx barrier is a chemical reaction barrier. This is not to be confused with the potential barrier between the metal and semiconductor interface of a Schottky diode which is defined as the difference between the work function of the metal in electron volts and the electron affinity of the semiconductor also expressed in electron volts.

For operation of a diode certain elements may not be shown in the top down view. For example, some missing elements may include a first electrode that forms a backside contact to the substrate 302 and leads to a voltage source. The polarity of the voltage may be changed across the diode to accomplish a reverse bias. A second contact on a contact pad 312 forms a topside contact to the sensor. The topside contact reads or applies a voltage to the top of the sensor. A voltage is applied across the topside contact to the backside contact. A forward current moves from the topside contact to the backside contact.

Figure 3B:
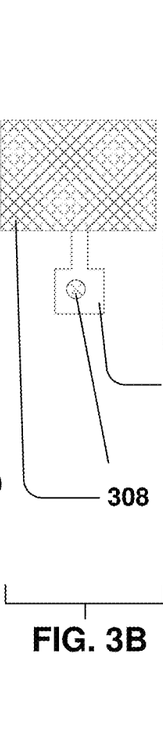
FIG. 3B illustrates an embodiment of a step in a fabrication process associated with gas sensors with contact pads.
Figures 3C, 3D:
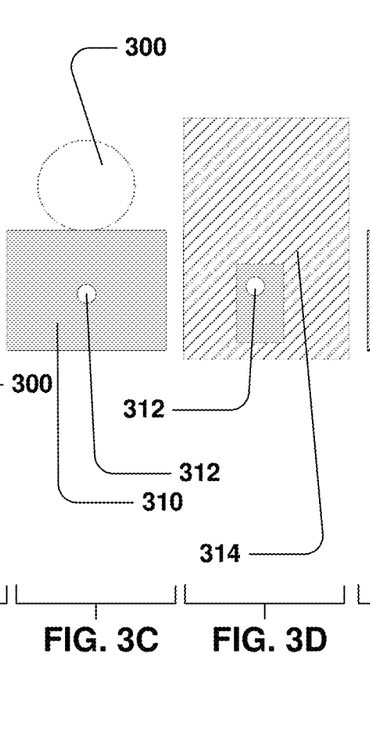
FIG. 3C illustrates an embodiment of a step in a fabrication process associated with gas sensors with contact pads.
FIG. 3D illustrates an embodiment of a step in a fabrication process associated with gas sensors with contact pads.

With reference to FIG. 3B, a first mask 308 is used on top of the metal layer 300 described in FIG. 3A. With reference to FIG. 3C and continuing reference to FIG. 3B, the first mask 308 dictates the size and location of an insulation layer 310. In one embodiment, the first mask 308 dictates a conduction path 312 where the insulation layer 310 is not applied and can be filled with a conducting material and/or compound. The first mask 308 utilizes a photolithographic process and/or the like to deposit the insulating layer 310 where the mask 308 does not cover the metal layer 300 such that the sensing area 306 in FIG. 3C of the metal layer 300 remains uncovered, i.e. able to be exposed to gas or the element to be sensed. In one embodiment, masks 304, 310, and 314 are for blocking the area from being deposited with films.

Figure 3E:
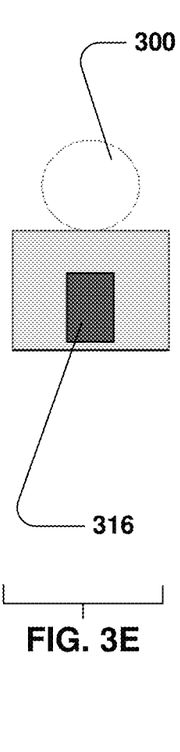
FIG. 3E illustrates an embodiment of a step in a fabrication process associated with gas sensors with contact pads.

With reference to FIG. 3D, a second mask 314 is used on top of the insulation layer 310 described in FIG. 3C. With reference to FIG. 3E and continuing reference to FIG. 3D, the second mask 314 dictates the size and location of a contact pad 316. In one embodiment, the deposition of the contact pad 316 includes filling the conduction path 312 with a conducting material and/or compound. The deposition of the contact pad 316 includes overlapping the conduction path 308 with a conducting material and/or compound. The second mask 314 utilizes a photolithographic process and/or the like to deposit the contact pad 316 where the second mask 314 does not cover the metal layer 300 such that the sensing area 306 of the metal layer 300 remains uncovered, i.e. able to be exposed to gas or the element to be sensed.

Figure 3F:
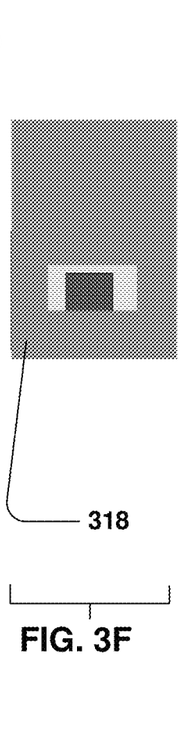
FIG. 3F illustrates an embodiment of a step in a fabrication process associated with gas sensors with contact pads.
Figure 3G:
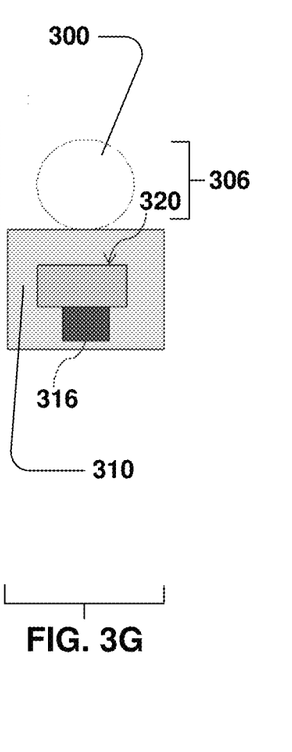
FIG. 3G illustrates an embodiment of a step in a fabrication process associated with gas sensors with contact pads.

With reference to FIG. 3F, a third mask 318 is used on top of the contact pad 316 described in FIG. 3E. With reference to FIG. 3G and continuing reference to FIG. 3F, the third mask 318 dictates the size and location of a second insulation layer 320. In one embodiment, the deposition of second insulation layer 320 includes overlapping the conduction path 312 and the portion of the insulation cover 316 that overlaps the top end of the conduction path 312 with an insulating material and/or compound. The second insulation layer 320 does not overlap a portion of the contact pad 316 such that an electrical connection can be wire bonded to the contact pad 316. The third mask 318 utilizes a photolithographic process and/or the like to deposit the second insulating layer 320 where the third mask 318 does not cover the metal layer 300 such that the sensing area 306 of the metal layer 300 remains uncovered, i.e. able to be exposed to gas or the element to be sensed. The resulting structure is a complete diode for sensing atmospheric conditions. After the second insulating layer 320 is deposited, wire bonding can attach an electrical wire to the contact pad 316 that is not covered by the second insulating layer 320.

In an exemplary embodiment, a complete basic sensor structure (diode-contact pad) is formed. Pd/PdOx metal/metal oxide is first laid on the SiC surface as a sensing layer. To avoid any stress caused by height differences underneath the basic layers, a SiO2 layer is deposited on top of the basic structure except the circular diode surface (for sensing), and a small area conduction path through on the contact pad (for connecting to the wire-bonding noble metal layer to be deposited next). A thicker layer (e.g., in one embodiment the thicker layer may be approximately 1 micron thickness) of noble metal (such as Pt or Pd) is deposited on the whole contact pad surface. A wire is bonded to the noble metal using wire-bonding. The metal surface with the wire bonding above the small area without SiO2 film is capped with another layer of SiO2 so that gas ions will not diffuse through the small area on the contact pad, i.e. no surface on the wire-bonding pad will function as another diode sensor surface.

In on embodiment, fabrication of the exemplary sensor can be conducted with a combination of photomasks and shadow masks to effectively develop the sensors. The combination of photomask and shadow mask approach can result in an applicable microsensor with a diode of 600 um radius, and a contact pad of 600 um×600 um area. Further, a set of photomasks can be designed (e.g., diode of 250 um radius, 300 um×300 um contact pad) for size reduction. Standard photolithography and appropriate semiconductor microfabrication process can be used for the fabrication.

The diode and contact base structure can be fabricated with a photomask for the metal layer with the rest of the fabrication conducted with shadow masks. The application of shadow masks avoids photolithography liftoff processes and avoids potential deactivation and contamination of SiC diode surface.

Figure 4:
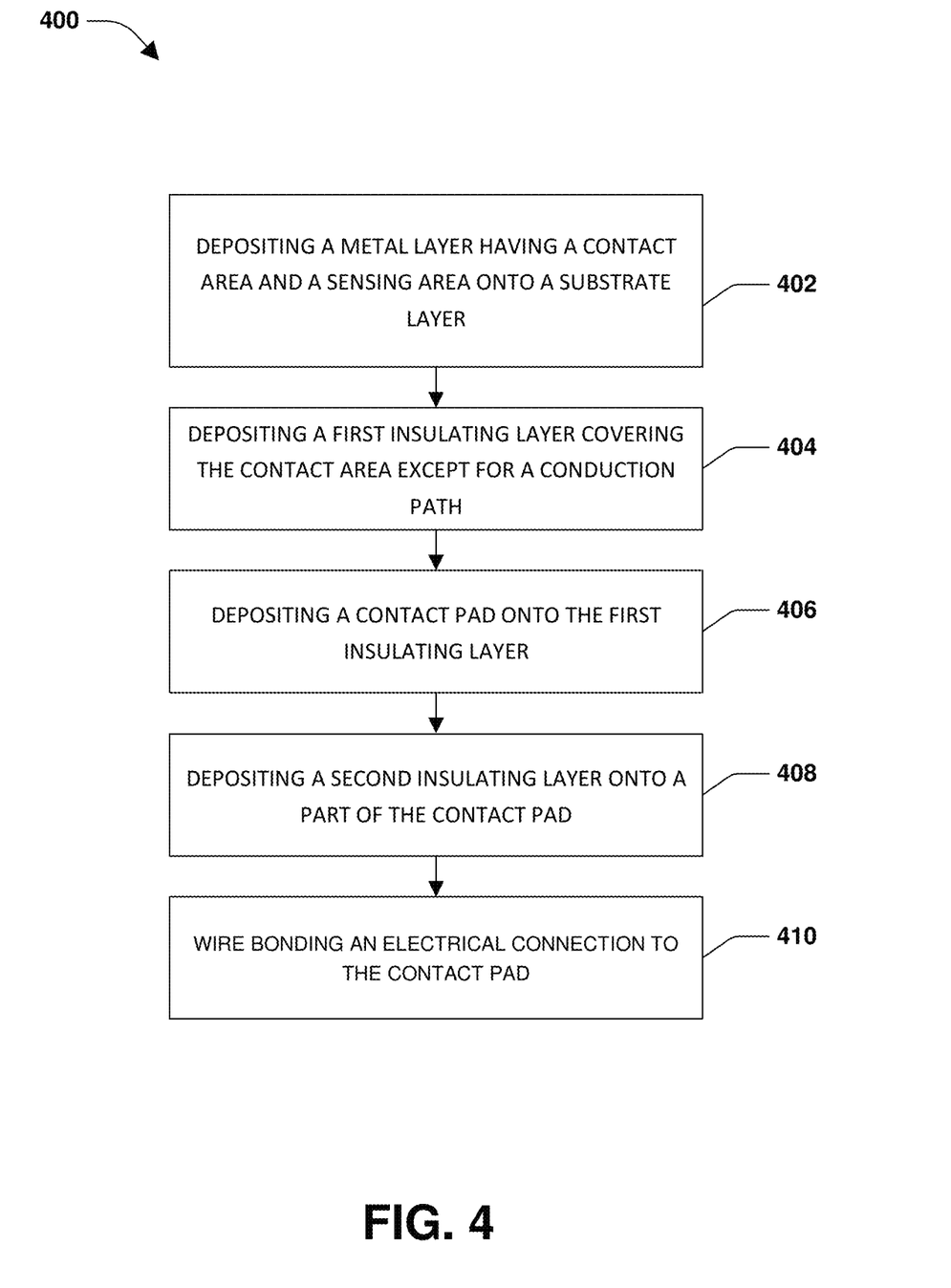
FIG. 4 illustrates an exemplary method for fabricating gas sensors with contact pads.

With reference to FIG. 4, a method 400 for fabricating a sensor with contact pad is depicted. At a step 402, a metal layer is deposited on a substrate layer. As described above, a metal oxide barrier layer may be deposited onto the substrate layer before the metal layer and the metal layer is deposited on top of the metal oxide layer. The deposition of the metal layer includes a mask such as a photomask or a shadow mask that details the size and shape of the metal layer. The metal layer includes a sensing area and a contact area.

At a step 404, a first insulating layer is deposited on the metal layer. As described above, the first insulating layer covers the entire contact area of the metal layer except for a conduction path. The conduction path has an area smaller the area of the first insulating layer. The deposition of the first insulating layer includes a photomask or a shadow mask that details the size and shape of the first insulating layer. The first insulating layer includes an insulating barrier that shields gases from diffusing into the contact area of the metal layer and a conduction path that does not shield the gases. As described above, after the deposition of the first insulating layer, the conduction path is hollow to be filled with conducting material in a further step as described in detail below.

At a step 406, a contact pad is deposited onto the first insulating layer. The contact pad is made of a conducting material. The deposition of the contact pad includes a photomask or a shadow mask that details the size and shape of the contact pad. While depositing the contact pad, the conduction path that is hollow is concurrently filled with the same conducting material of the contact pad. The filled conduction path is an electrical connection between the contact area of the metal layer and the contact pad traversing through the first insulating layer.

At a step 408, a second insulating layer is deposited onto part of the contact pad. The deposition of the second insulating layer includes a photomask or a shadow mask that details the size and shape of the second insulating layer. As described above, the second insulating layer is made of an insulating material with sufficient thickness to also serve as a diffusion barrier. The second insulating layer is deposited onto the part of the contact pad where the contact pad meets the conduction path such that it shields the pad from gases diffusing into the contact area of the metal layer. The second insulating layer is deposited onto a portion of the contact pad so as to still to allow for wire bonding of an electrical connection described below.

At a step 410, an electrical connection is wire bonded to the part of contact pad that is not insulated, i.e. not covered by the second insulating layer. The electrical connection can read a voltage at the contact pad and is the same voltage at the metal layer due to the conduction path conducting between the contact pad and the metal layer.

The exemplary structure as described herein has been described as an exemplary diode. However, the innovation is not limited to only such a structure. Other structures are contemplated such as capacitors, transistors, etc. Likewise, the structure is described as sensing hydrogen/hydrocarbon gas, however, other gases and other uses are contemplated. This is a multiuse method to allow contacts to gas sensors in general without direct wire bond contact to the sensing surface.

While for purposes of simplicity of explanation, illustrated methodologies are shown and described as a series of blocks. The methodologies are not limited by the order of the blocks as some blocks can occur in different orders and/or concurrently with other blocks from that shown and described. Moreover, less than all the illustrated blocks may be used to implement an example methodology. Blocks may be combined or separated into multiple components. Furthermore, additional and/or alternative methodologies can employ additional, not illustrated blocks. The methods described herein are limited to statutory subject matter under 35 U.S.C. § 101.

To the extent that the term "includes" or "including" is employed in the detailed description or the claims, it is intended to be inclusive in a manner similar to the term "comprising" as that term is interpreted when employed as a transitional word in a claim.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the disclosure is not limited to the specific details, the representative apparatus, and illustrative examples shown and described. Thus, this application is intended to embrace alterations, modifications, and variations that fall within the scope of the appended claims, which satisfy the statutory subject matter requirements of 35 U.S.C. § 101.

Various operations of embodiments are provided herein. The order in which one or more or all of the operations are described should not be construed as to imply that these operations are necessarily order dependent. Alternative ordering will be appreciated based on this description. Further, not all operations may necessarily be present in each embodiment provided herein.

As used in this application, "or" is intended to mean an inclusive "or" rather than an exclusive "or". Further, an inclusive "or" may include any combination thereof (e.g., A, B, or any combination thereof). In addition, "a" and "an" as used in this application are generally construed to mean "one or more" unless specified otherwise or clear from context to be directed to a singular form. Additionally, at least one of A and B and/or the like generally means A or B or both A and B. Further, to the extent that "includes", "having", "has", "with", or variants thereof are used in either the detailed description or the claims, such terms are intended to be inclusive in a manner similar to the term "comprising".

Further, unless specified otherwise, "first", "second", or the like are not intended to imply a temporal aspect, a spatial aspect, an ordering, etc. Rather, such terms are merely used as identifiers, names, etc. for features, elements, items, etc. For example, a first channel and a second channel generally correspond to channel A and channel B or two different or two identical channels or the same channel.

Although the disclosure has been shown and described with respect to one or more implementations, equivalent alterations and modifications will occur based on a reading and understanding of this specification and the annexed drawings. The disclosure includes all such modifications and alterations and is limited only by the scope of the following claims.

What is claimed is:

1. A method for fabricating a gas sensor, comprising:
   depositing a metal layer on a substrate layer, the metal layer including a sensing area and a contact area;
   depositing a first insulating layer on the metal layer, wherein the first insulating layer covers substantially the entirety of the contact area and not the sensing area, wherein the first insulating layer includes a conduction path extending from a first surface thereof to a second surface thereof, the conduction path overlapping the contact area;
   depositing a contact pad onto the first insulating layer such that the contact pad overlaps the conduction path; and
   depositing a second insulating layer onto the contact pad such that the second insulating layer overlaps the conduction path.

2. The method of claim 1, wherein the contact pad has an insulated area, which is covered by the second insulating layer, that prevents diffusion through the contact pad, the conduction path, or the contact area of the metal layer, and the second insulating layer also leaves an exposed area of the contact pad.

3. The method of claim 2, further comprising connecting the exposed area of the contact pad to a wire from which an electrical signal can be determined or applied.

4. The method of claim 2, wherein the conduction path in the first insulation layer is hollow immediately after depositing the first insulation layer, wherein the conduction path is filled while depositing the contact pad, and wherein the contact pad and the conduction path form a single body.

5. The method of claim 1, further comprising depositing a metal oxide layer on the substrate layer prior to depositing the metal layer.

6. The method of claim 5, wherein the depositing of the metal oxide layer comprises sputtering a first metal onto the substrate layer in an oxygen atmosphere such that the metal oxide layer has a first thickness.

7. The method of claim 6, wherein the depositing of the metal layer comprises sputtering a material onto the metal oxide layer such that the metal layer has a second thickness, wherein the material is a metal or a metal alloy.

8. The method of claim 7, wherein the second thickness is greater than the first thickness.

9. The method of claim 8, wherein the metal or the metal alloy is selected from the group consisting of Pt, Pd, Au, Ir, Ag, Ru, Rh, In, Os, Cr, Ti, and alloys thereof.

10. The method of claim 9, wherein the second thickness is approximately 1000 angstroms.

11. The method of claim 9, wherein the second thickness is between 450 and 500 angstroms.

12. The method of claim 5, wherein the depositing of the metal oxide layer comprises evaporating palladium oxide onto the substrate layer.

13. The method of claim 1, further comprising connecting a side of the substrate layer opposite to the metal layer to an electrode in contact with a voltage source.

14. The method of claim 1, wherein depositing the first insulation layer comprises depositing a first photolithographic mask onto the metal layer, wherein the first photolithographic mask includes a first portion covering the sensing area and a second portion covering the contact area only in a region corresponding to a desired location of the conduction path, wherein the first and second portions are not connected to one another within the first photolithographic mask.

15. The method of claim 14, wherein depositing the second insulation layer comprises depositing a second photolithographic mask onto the contact pad, wherein the second photolithographic mask includes an opening overlapping a portion of the contact pad and the conduction path.

16. A method for fabricating a gas sensor, comprising:
    providing a substrate having a metal oxide layer disposed on a surface thereof and a metal layer disposed on the metal oxide layer, wherein the metal layer has a shape corresponding to the metal oxide layer and includes a sensing area and a contact area;

depositing a first insulating layer onto the metal layer, wherein the first insulating layer covers at least a portion of the contact area, wherein, immediately after deposition, the first insulating layer includes an opening extending from the metal layer to a surface of the first insulating layer;

depositing an electrically conductive material into the opening and onto the surface of the first insulating layer to form a conduction path within the first insulating layer and a contact pad on the surface of the first insulating layer; and depositing a second insulating layer onto the contact pad such that the second insulating layer overlaps the conduction path.

17. The method of claim 16, wherein the contact pad overlaps substantially the entirety of the first insulating layer.

18. The method of claim 17, wherein the second insulating layer overlaps only an insulated portion of the contact pad to form a connection portion of the contact pad not covered by the second insulating layer.

19. The method of claim 18, further comprising connecting the connection portion of the contact pad to a voltage source.

20. The method of claim 19, wherein the metal layer is constructed of a material selected from the group consisting of Pt, Pd, Au, Ir, Ag, Ru, Rh, In, Os, Cr, Ti, and alloys thereof.

* * * * *